(12) United States Patent
Fukuzuno et al.

(10) Patent No.: US 6,251,659 B1
(45) Date of Patent: Jun. 26, 2001

(54) BIOLOGICAL SAMPLE TREATING APPARATUS (75) Inventors: Shinichi Fukuzuno, Hitachinaka; Norie Maeuchihara, Ichikawa; Toshinari Sakurai, Hitachinaka; Kenji Yasuda, Nakano-ku, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/419,918

(22) Filed: Oct. 18, 1999

(30) Foreign Application Priority Data

Oct. 19, 1998 (JP) .................................................. 10-296605

(51) Int. Cl.$^7$ .................................................. C12M 1/36
(52) U.S. Cl. .................................. 435/286.2; 435/286.4; 435/287.3; 435/303.1; 422/65
(58) Field of Search ........................ 165/266, 267, 165/86; 435/286.1, 286.2, 286.4, 287.3, 303.1; 422/63, 65; 219/521

(56) References Cited

U.S. PATENT DOCUMENTS

| 4,584,275 | * | 4/1986 | Okano et al. | 435/290 |
| 4,865,986 | * | 9/1989 | Coy et al. | 435/290 |
| 5,055,408 | * | 10/1991 | Higo et al. | 436/48 |
| 5,446,263 | * | 8/1995 | Eigen et al. | 219/521 |
| 5,635,397 | * | 6/1997 | Futschik et al. | 435/286.1 |
| 6,146,882 | * | 11/2000 | Uematsu et al. | 435/303.1 |

FOREIGN PATENT DOCUMENTS

| 3-224474 | * | 10/1991 | (JP) . |
| 4-99477 | * | 3/1992 | (JP) . |
| 8-15437 | * | 2/1996 | (JP) . |

* cited by examiner

Primary Examiner—David A. Redding
(74) Attorney, Agent, or Firm—Mattingly, Stanger & Malur, P.C.

(57) ABSTRACT

A rectangular-shaped holder containing sample solution is moved within a temperature adjusting box by a feeder. Then, the holder is moved by another feeder to the direction substantially perpendicular to the longitudinal direction of the holder by a length equal to the width of the single holder. The holders thus sequentially fed within the temperature adjusting box are disposed within the box in a closely contacted state from one another. There are three holders within the temperature adjusting box in advance and four holders are stayed within the box. Rectangular-shaped four heaters are disposed within the temperature adjusting box such that the heating temperature thereof is controlled by a temperature adjusting controller. A compensation heater controlled by a temperature compensating controller compensates for a heat quantity shifted to the holder having been newly housed within the temperature adjusting box from the holders already housed within the temperature adjusting box.

11 Claims, 5 Drawing Sheets

BIOLOGICAL SAMPLE TREATING APPARATUS

BACKGROUND OF THE INVENTION

The present invention relates to an apparatus for automatically performing the temperature treating processing of a biological sample and, more particularly, relates to, in the field of diagnosing and inspecting a gene, an apparatus for automatically dissolving a biological sample in the operation for extracting, isolating and refining a gene from a biological sample, in particular, a mycobacterium species among bacteria.

In recent years, in accordance with the development of the gene research, the diagnosis of gene such as infectious disease, cancer, hereditary disease or the like and the various methods using the gene such as appraisal or analysis of parent and children, inspection for identifying a person or the like have been widely employed.

The gene analysis is considered to be increasingly developed from now since the gene analysis is superior in the expeditiousness, the detection of small amount and the speedy detection in comparison with the conventional cultivation assays of bacteria and the conventional immunological assays using the antigen-antibody reaction or the like. In particularly, in the field of the medical gene analysis, in accordance with the increase of the infectious disease such as human immunodeficiency virus (HIV), hepatitis B virus and hepatitis C virus (HBV, HCV), tuberculosis or the like, the development of the analysis kit or the like has been expanded rapidly and the demands for the mass processing of samples has been increased.

In this manner, since the gene analysis is an excellent analysis method, the gene analysis has been put to practical use. However, the gene analysis is complicated and hence a skilled person is required to perform the analysis. In such a circumstance, it is has been desired to perform the gene analysis automatically in view of the simplicity, the labor saving, the mass processing, and the safety of a person in charge of the analysis.

The aforesaid gene inspection is performed by the four processes, that is, (1) the process of extracting nucleic acid from an specimen, (2) the process of isolating the nucleic acid, (3) the process of DNA amplification (there are some method such as the DNA probe method which do not require this process), and (4) the process of detecting the target nucleic acid. In the aforesaid four processes, the automatic devices for performing the processes (3) and (4) automatically have been developed.

Further, the automatic devices for performing the aforesaid processes (1) and (2) automatically are disclosed in Japanese Patent Publication No. Hei-8-15437, Japanese Patent Kokai (Unexamined Laid-Open) No. Hei-4-99477 and Japanese Patent Kokai (Unexamined Laid-Open) No. Hei-3-224474.

However, the aforesaid automatic devices performs the process of isolating nucleic acid from a cell mainly as to a virus. Since the viruses such as HIV, HBV, HCV and the cells of animals are covered by relatively weak cell membranes or coat protein, nucleic acid can be isolated easily from a cell. For example, virus RNA can be obtained in a manner that guanidine hydrochloride as the denaturant is added to serum and then heated for 10 minutes at 60° C. (see Since the bacteria are covered by cell walls, there is a case requiring particular process such as enzymatic treatment, heat processing, mechanical grinding breakage, sonication or the like. In particular, since a tuberculosis includes much mycolic acid within cell walls to form the strong cell walls, it is difficult to extract a gene therefrom. In this case, the aforesaid devices are required to perform the breakage processing of a cell body manually.

BRIEF SUMMARY OF THE INVENTION

As described above, the conventional biological sample automatic processing apparatus can perform the biomolecule extraction process automatically only in the case where biological samples are ones in which a biomolecule can be isolated easily from a cell thereof by using the protein denaturant or detergent, but can not perform the biomolecule extraction process automatically in the case where biological samples are ones such as bacteria each requiring the particular processing at the time of isolating a biomolecule therefrom.

Accordingly, an object of the present invention is to provide a biological sample automatic processing apparatus which can obviate the aforesaid problem of the conventional biological sample automatic processing apparatuses.

Another object of the present invention is to realize a biological sample automatic processing apparatus which includes a temperature adjuster performing such a temperature processing that a sample solution containing treating liquid such as enzyme solution, detergent solution, organic solution, acid solution, alkaline solution or the like for isolating biomolecule from a biological sample is held at a constant temperature during a constant time period and to further includes a mechanism for moving the biological sample for the automatic processing.

In order to attain the aforesaid objects, the present invention is arranged in the following manner.

(1) A biological sample processing apparatus, comprising:
a temperature adjuster for keeping a plurality of holders at a setting temperature while moving the plurality of holders each supporting a container receiving biological sample solution therein; and
at least one temperature compensation section which, in a stage before a new holder moves into the temperature adjuster, controls temperature of the plurality of holders for a constant time period so as to be higher than a setting temperature when the setting temperature is higher than a temperature in the stage, and controls the temperature of the plurality of holders for a constant time period so as to be lower than the setting temperature when the setting temperature is lower than a temperature in the stage, wherein the at least one temperature compensation section can control the temperature of the plurality of holders independently from the temperature adjuster, and wherein the plurality of holders are disposed within the temperature adjuster in a closely contacted state from one another Thus, in the present invention, since the holders are arranged in a closely contacted state from one another at the time of moving the holders within the temperature adjuster, heat can be transferred through the mutual contact surfaces of the holders. Thus, when the holder newly moves into the temperature adjuster, heat also can be transferred to the new holder from the holders having been stayed within the temperature adjuster, so that the temperature of the new holder can quickly reach the constant temperature.

Further, since the holders are disposed in the closely contacted state from one another within the temperature adjuster, the degree of the unevenness of temperature among the holders can be reduced and so the temperature among the holders can be made almost uniform.

Furthermore, since, in the stage before the new holder moves into the temperature adjuster, heat quantity transferred among the holders is compensated by the temperature compensation section provided independently from the temperature adjuster, the temperature of the holders can be controlled quickly and with high accuracy.

(2) Preferably, in the aforesaid the arrangement (1), the biological sample processing apparatus further comprising a pipetting means for dispensing treating liquid within the containers, wherein the apparatus repeatedly performs for an arbitrary number of times a process of dispensing the treating liquid within the containers, a process of moving the holders and a process of keeping the containers at a constant temperature for a constant time period.

(3) Preferably, in the aforesaid the arrangement (1), the at least one temperature compensation section controls a temperature of the holders in correspondence with a movement of the new holder.

(4) Preferably, in the aforesaid the arrangement (2), the treating liquid contains detergent.

(5) Preferably, in the aforesaid the arrangement (2), the treating liquid contains sodium hydroxide, potassium hydroxide or ammonium hydroxide.

(6) Preferably, in the aforesaid the arrangement (2), the treating liquid contains lysozyme, pronase or lipase.

(7) Preferably, in the aforesaid the arrangement (2), the treating liquid contains chelating agent.

(8) Preferably, in the aforesaid the arrangement (1), the treating liquid is a mixture of sodium hydroxide, potassium hydroxide and ammonium hydroxide, or a mixture of lysozyme, pronase and lipase.

(9) Preferably, in the aforesaid the arrangement (2), the treating liquid contains chaotropic agent.

(10) Preferably, in the aforesaid the arrangement (1), the biological sample contains microorganism.

(11) Preferably, in the aforesaid the arrangement (1), the microorganism is mycobacteriaceae.

DETAILED DESCRIPTION OF THE INVENTION

Figure 1:
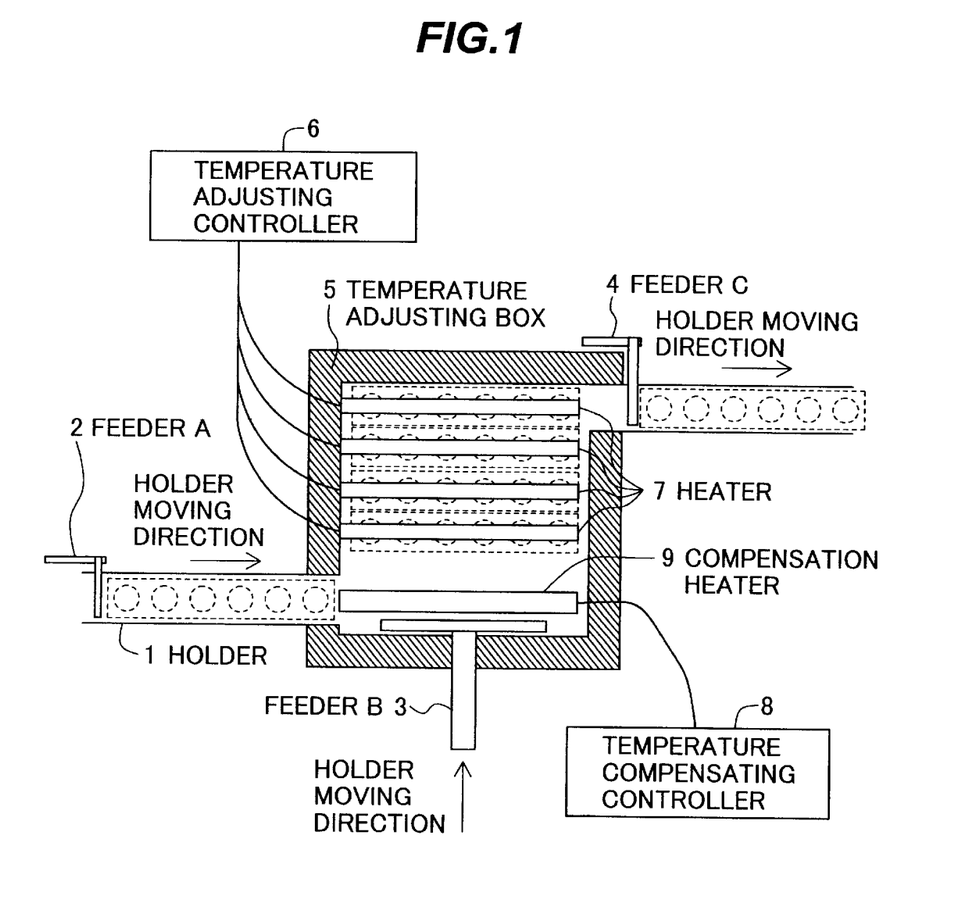
FIG. 1 is a schematic diagram showing the configuration of a main portion of a biological sample automatic processing apparatus according to an embodiment of the present invention.

FIG. 1 is a schematic diagram showing the configuration of a main portion of a biological sample automatic processing apparatus according to an embodiment of the present invention.

In FIG. 1, a rectangular-shaped holder 1 containing sample solution is moved along the longitudinal direction of the holder 1 by a feeder A2 and then placed within a temperature adjusting box 5. Then, the holder 1 is moved by a feeder B3 to the direction substantially perpendicular to the longitudinal direction thereof, that is, the upper direction in the figure by a length equal to the width of the single holder 1. The holders 1 thus sequentially fed within the temperature adjusting box 5 are disposed within the temperature adjusting box 5 in a manner that the side walls of the holders 1 along the longitudinal direction thereof are closely contacted from one another. Of the holders 1 within the temperature adjusting box 5, the holder 1 disposed at the uppermost position in the figure is moved to the longitudinal direction of the holder 1 by a feeder C4 and exhausted outside of the temperature adjusting box 5.

There are three holders within the temperature adjusting box 5 in advance. The holders 1 are fed one by one within the temperature adjusting box 5 and exhausted therefrom by the feeders A2, B3 and C4 in a manner that four holders are stayed or remained within the temperature adjusting box 5. The time period during which each holder 1 is stayed within the temperature adjusting box 5 is a temperature treating setting period. The temperature adjustment is performed in the following manner. That is, rectangular-shaped four heaters 7 are disposed at the positions corresponding to the four holders 1 stayed within the temperature adjusting box 5, respectively, and these four heaters 7 are controlled at the treating setting temperature by a temperature adjusting controller 6. Each of the heaters 7 according to the embodiment does not only contain a heater but also contains a cooler.

In the thus configured biological sample automatic processing apparatus, it is considered to use a block heater (dry bath), a constant temperature water bath, a blowing constant temperature bath, a constant temperature air bath or the like as the temperature adjuster. However, the constant temperature water bath employs antifreeze solution, water or oil and such solution adheres to sample containers and is moved together with the containers, so that the atmosphere is likely polluted. Thus, the constant temperature water bath is not suitable for the biological sample automatic processing apparatus. Further, the constant temperature air bath has a problem that it takes much time to adjust temperature of a sample and the controlled temperature is likely uneven within the bath. Thus, the constant temperature air bath is also not suitable for the biological sample automatic processing apparatus.

Although the blowing constant temperature bath can eliminate the unevenness of the temperature within the bath, there is problems that the temperature becomes uneven between a sample directly exposed to the wind and a sample not exposed to the wind and that the arrangement of the apparatus is complicated or restricted depending on the blowing direction.

In view of the aforesaid matters, it is considered that the block heater is suitable for the temperature control, simplification of the apparatus and economization. Thus, the embodiment employs the block heater.

A compensation heater 9 which is controlled by a temperature compensating controller 8 is disposed at the position corresponding to the holder 1 just having been newly housed within the temperature adjusting box 5 by the feeder A2. A quantity of heat to be shifted to the holder 1 having been newly housed within the temperature adjusting box 5 from the holders 1 already housed within the temperature adjusting box 5 is compensated for a constant time period by the compensation heater 9 prior to the time point where the holder 1 to be newly housed within the temperature adjusting box 5 contacts to the holder 1 already housed within the temperature adjusting box 5. That is, the temperature compensating controller 8 controls the operation of the compensation heater 9 for heating the holder 1 in synchronism with the housing operation of the holder 1 into the temperature adjusting box 5.

The bottom wall of the temperature adjusting box 5 is made of material with good thermal conductivity such as aluminum or the like and so there appears temperature gradient for a predetermined time period due to the aforesaid heating control.

At the time of performing the heating control, it is important to prevent such a matter that temperature of the sample solution held by the holders 1 already housed within the temperature adjusting box 5 changes from the setting temperature due to the aforesaid temperature gradient. The heat transmission speed from the holder 1 to the sample solution through the biological sample container is slower than the heat transmission speed from the heaters 7 within the temperature adjusting box 5 to the holder 1 with the higher thermal conductivity and the heat transmission speed between the holders 1. Thus, there is the time difference between the time period required for the heat transmission from the holder 1 to the sample solution and that from the heater 7 to the holder 1 or between the holders 1. The temperature compensation is performed during this time difference, whereby the aforesaid temperature change of the sample solution held by the holders 1 can be prevented.

FIG. 1 is illustrated simply so as to merely show the major portion of the present invention. The biological sample processing apparatus may be arranged to provide a temperature adjusting mechanism and a temperature reserving structure at the side wall or upper wall of the temperature adjusting box 5 or the inlet portion of the holder 1.

Figure 2:
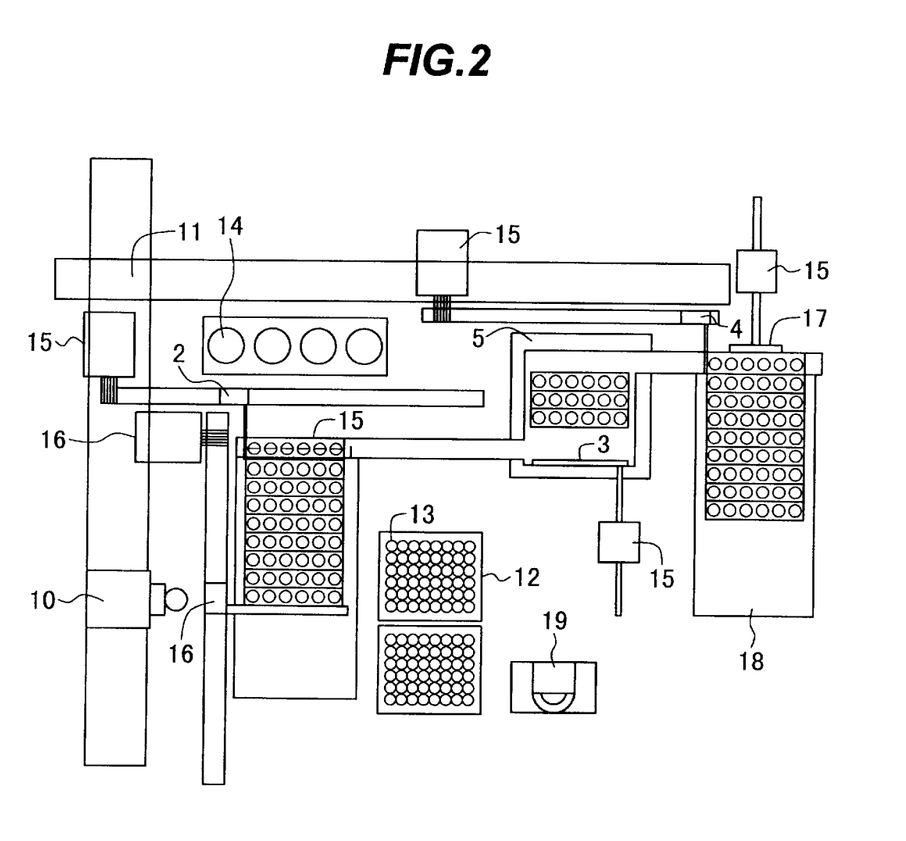
FIG. 2 is a diagram showing a biological sample processing apparatus having a pipetting mechanism according to an embodiment of the present invention.

FIG. 2 is a diagram showing a biological sample processing apparatus having a pipetting mechanism according to an embodiment of the present invention. In FIG. 2, a pipetting mechanism 10 can move freely on an X–Y arm 11 and also can be driven to a Z direction (direction perpendicular to the sheet of the figure). The pipetting mechanism 10 inserts a chip 13 on a chip rack 12 into its tip end, then extracts treating liquid 14 partially therefrom and adds the extracted treating liquid to the sample container on the holder 1. Plural kinds of treating liquid may be arranged as the treating liquid 14 and the adding position of the treating liquid may be set arbitrarily.

When the addition of the treating liquid into the sample container on the holder 1 has been completed, the holder 1 is shifted within the temperature adjusting box 5 by the feeder A2 which is driven by a feed motor 15, and then is brought into close contact by the feeder 3B with the holder 1 already placed within the temperature adjusting box 5, whereby the temperature processing of the sample solution is started. At this time, the holder 1 is shifted to the feeder A2 direction by a length of one holder by a feeder D16 and is standing by until the next pipetting operation so that the standing-by time period becomes a time period calculated based on the processing time.

When the temperature processing of the sample solution has been completed, the holder 1 is taken out of the temperature adjusting box 5 by the feeder C4 and placed on a holder rack 18 by a feeder E17. Incidentally, it is possible to add the treating liquid within the sample container of the holder 1 at this stage, that is, the holder 1 just placed on the holder rack 18.

The chip 13 having been used is separated from the tip end of the pipetting mechanism 10 and collected by a chip collecting section 19, and the pipetting mechanism 10 is standing by until the next operation.

A multiplicity of samples can be processed automatically and continuously by repeatedly performing the aforesaid operations.

Figure 3:
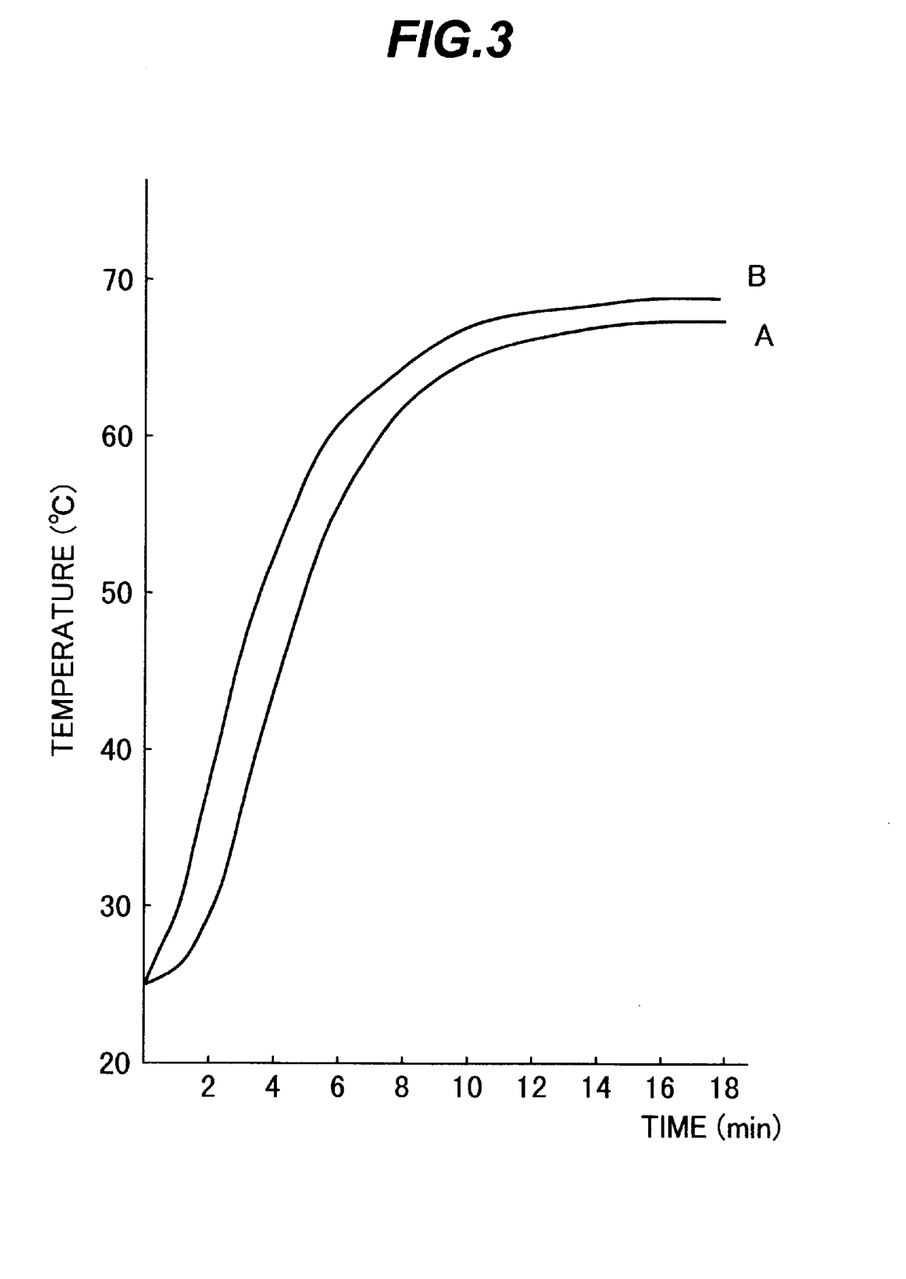
FIG. 3 is a graph showing the relation between the temperature increase properties of the sample solution when the holders are disposed in a contacted state and non-contacted state.

FIG. 3 is a graph showing the relation between the temperature increase property (curve A) of the sample solution held by the holders which are disposed with an interval of 1 mm to each other when the holders are piled up and the temperature increase property (curve B) of the sample solution held by the holders which are disposed closely from one another when the holders are piled up. In the figure, an ordinate represents the temperature of the sample solution and an ordinate represents the time (minute).

As clear from the graph shown in FIG. 3, the temperature increase rate of the temperature increase property (the curve A) of the sample solution held by the holders disposed closely is larger than that of the temperature increase property (the curve B) of the sample solution held by the holders disposed with the interval of 1 mm, that is, the time period required for increasing the temperature to 60° C. is higher in the former case (the curve A) than the latter case(the curve B). In particular, the temperature increase rate during one minute after the starting of the heating operation is remarkably different between the temperature increase properties of the curves A and B. This is because it is considered that the heat quantity transferred from the side wall of the holder to that of the adjacent holder largely contributes to the initial temperature increase rate.

Figure 4:
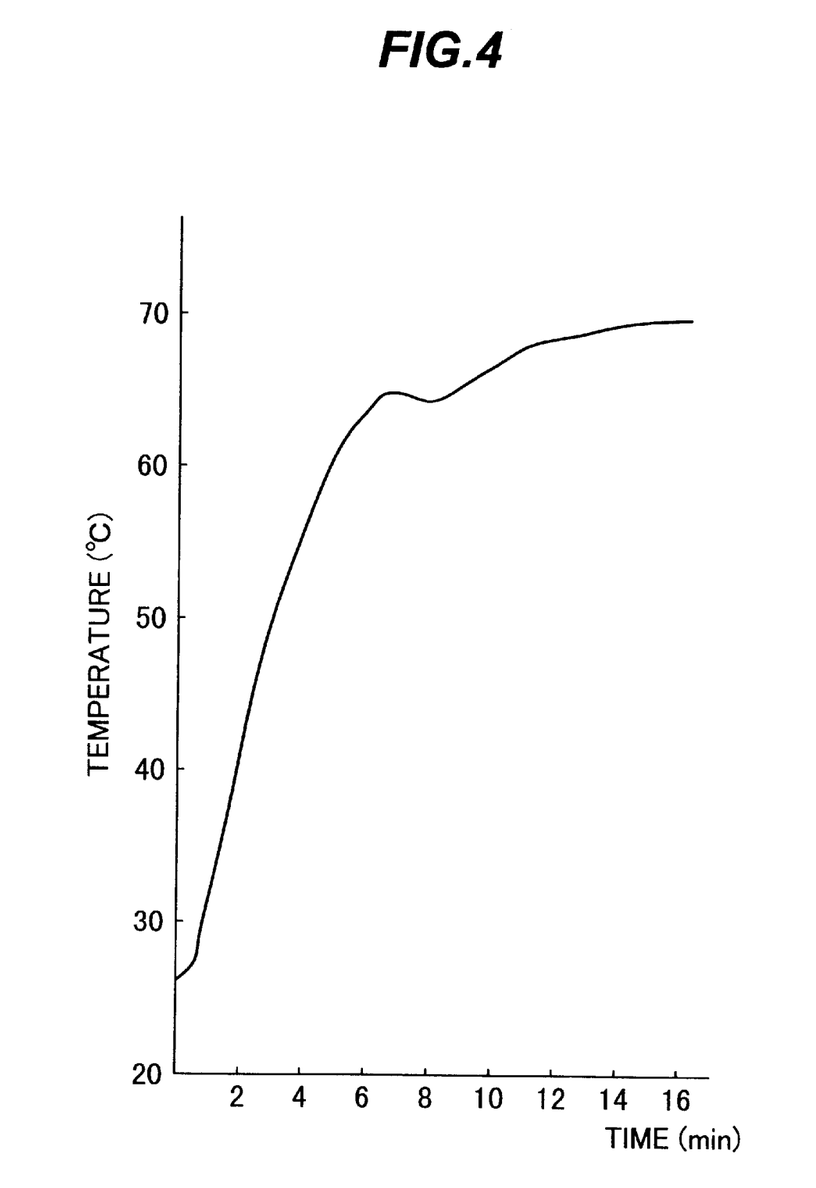
FIG. 4 is a graph showing the liquid temperature increase property of the sample solution in the case where the temperature compensation section is not employed in the heating process, when the holders are disposed in a contacted state.

FIG. 4 is a graph showing the liquid temperature increase property of the sample solution held by the holders having been stayed within the temperature adjusting box 5 when a new holder is moved within the temperature adjusting box 5, in the case where the temperature compensation section is not employed and the holders within the temperature adjusting box 5 are disposed closely. Upon the lapse of 6 minutes and half after the starting of the heating operation, when the new holder is brought into contact with the holder having been stayed within the temperature adjusting box 5, the liquid temperature of the sample solution held by the holder having been stayed within the temperature adjusting box 5 decreased by about 1° C. This is because the heat is transferred from the holders having been stayed within the temperature adjusting box 5 to the new holder having lower temperature than the former ones, as anticipated from the temperature increase properties shown in FIG. 3.

Figure 5:
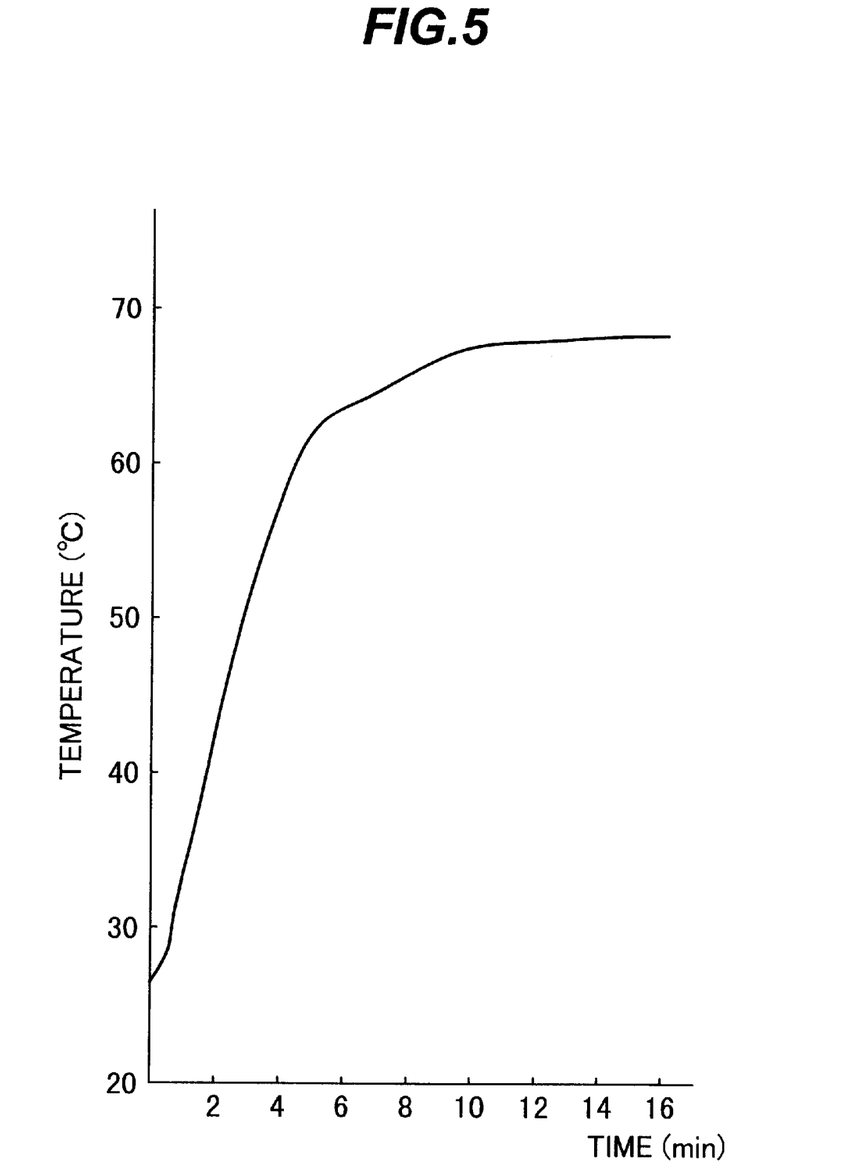
FIG. 5 is a graph showing the liquid temperature increase property of the sample solution in the case where the temperature compensation section is employed in the heating process, when the holders are disposed in a contacted state.

FIG. 5 is a graph showing the liquid temperature increase property of the sample solution held by the holders having been stayed within the same temperature adjusting box 5 as that used in the case of FIG. 4 when a new holder is moved within the temperature adjusting box 5, in the case where the temperature compensation section (the temperature compensating controller 8 and the compensation heater 9) according to the present invention is employed and the holders within the temperature adjusting box 5 are disposed closely.

In FIG. 5, when the new holder is brought into contact with the holder having been stayed within the temperature adjusting box 5 upon the lapse of 6 minutes after the starting of the heating operation, although the liquid temperature increase rate is slightly decreased, the liquid temperature is not decreased. Thus, it is considered that the temperature compensation effect was obtained by employing the temperature compensation section according to the present invention.

As described above, according to the embodiment of the present invention, it is possible to realize the biological sample automatic processing apparatus which includes the temperature adjuster for performing such a temperature processing of keeping, at constant temperature during a constant time period, the sample solution containing the treating liquid such as enzyme solution, surface active agent solution, organic solution, acid aqueous solution, alkaline aqueous solution or the like for isolating biomolecule from a biological sample, and the mechanism for automatically moving the biological sample for the automatic processing.

In the arrangement where the holders are not disposed in closely contacted state within the temperature adjusting box like the prior art, the heat is likely transferred or shifted from the surfaces where the heaters and the holders are contacted, that is, mainly the bottom surfaces, side surfaces and upper surfaces of the holders.

In contrast, in the arrangement where the holders are disposed in closely contacted state from one another within the temperature adjusting box 5 (temperature adjuster) at the time of sequentially shifting the holders 1 one by one within the temperature adjusting box 5 like the present invention, the heat is further likely transferred or shifted from the mutual contact surfaces of the adjacent holders. Thus, in the arrangement of the present invention, when the new holder 1 is moved into the temperature adjusting box 5, since the heat is further transferred from the holders 1 having been stayed within the temperature adjusting box 5 to the new holder 1, the liquid temperature of the sample solution held by the new holder 1 can be increased to the constant temperature quickly.

Further, in the arrangement of the present invention, since the holders 1 are disposed in closely contacted state from one another within the temperature adjusting box 5, the degree of the unevenness of the temperature among the holders 1 within the temperature adjusting box 5 can be reduced and the temperature of the holders can be made uniform. However, since the heat is transferred from the holders 1 having been stayed within the temperature adjusting box 5 to the new holder 1, the temperature of the holders having been stayed within the temperature adjusting box 5 decreases.

In order to prevent such decrease of the temperature, in the arrangement of the present invention, the temperature compensation section (8, 9) is provided at the portion of the temperature adjusting box 5 separately from the main body of the temperature adjusting box 5 into which the new holder 1 moves, thereby to compensate the heat quantity shifted among the holders. Thus, it becomes possible to perform the temperature control quickly with high accuracy.

In this arrangement, since the compensation heater is arranged to have the continuous surface, if the compensation heater is kept at the compensation temperature for more than the constant time period, the accuracy of the setting temperature of the main body of the temperature adjusting box will be degraded. Thus, the time period during which the compensation heater is kept at the compensation or control temperature is set in interlocking with the shift of the holder. Incidentally, the setting temperature and the setting time period are determined in accordance with the capacity of the heater, the size of the holder and the temperature environment.

In the embodiment of the biological sample processing apparatus having the pipetting mechanism shown in FIG. 2, the biological sample processing apparatus is arranged to include the temperature adjusting box 5 (temperature adjuster) capable of keeping the temperature while continuously moving the holders 1 holding the biological sample containers and the pipetting mechanism 10 for adding the cell treating liquid 14 within the biological sample containers. Further, the embodiment is arranged to include the following processes: (1) the process of dispensing the treating liquid 14 within the biological sample containers, (2) the process of moving the holder 1 to the temperature adjusting box 5 (temperature adjuster), and (3) the process of keeping the temperature of the biological sample containers within the temperature adjusting box 5 at the constant temperature during the constant time period.

In this embodiment, the aforesaid processes (1), (2) and (3) may be repeatedly performed for an arbitrary number of times, and the execution order of the processes (1), (2) and (3) may be changed, and further some of the processes (1), (2) and (3) may be combined together. Further, after the process (3), the sample may be kept at the constant temperature in the following process 1) or 2) by another temperature adjuster provided independently from the temperature adjuster 5. That is, for example, the process 1) is one of adding sodium dodecyl sulfate and sodium hydroxide to a cell body and keeping the temperature for a constant time period, and the process 2) is one of adding enzyme solution such as lysozyme, lipase, subtilisin or the like to a cell, then the enzyme reaction is performed sufficiently by the temperature keeping process, and thereafter nucleic acid is isolated from the cell body by using detergent such as sodium dodecyl sulfate, polyoxyethylene octylphenyl ether or the like.

The biological sample used in the embodiment may be a cellular piece such as sputum, urine, feces, blood, cerebrospinal fluid, hair, organ, skin, bone or the like, or may be a microorganism (including mycobacteriaceae), virus, protozoa or the like. The biomolecule used in the embodiment may be DNA, RNA, mRNA, protein or the like.

The holders 1 for holding the containers containing the biological sample therein may be made of material, which is high in thermal conductivity and capable of molding, such as metal, in particular, aluminum or the like.

The surface active agent solution may be used as the treating liquid for isolating the biomolecule from the biological sample. The biological sample solution used in the present invention may be sodium dodecyl sulfate, sodium lauryl sulfate, sodium N-lauroyl sarcosinate, polyoxyethylene (10) octyl phenyl ether, polyoxyethylene (9) octyl phenyl ether, polyoxyethylene sorbitan monolaurate or the like. However, the biological sample solution used in the present invention is not limited to those solution.

The enzyme solution may be used as the treating liquid for isolating the biomolecule from the biological sample. The enzyme solution used in the present invention may be lysozyme, proteinase K, pronase, subtilisin or the like. However, the enzyme solution used in the present invention is not limited to those solution.

The organic solution may be used as the treating liquid for isolating the biomolecule from the biological sample. The organic solution used in the present invention may be ethanol, phenol, chloroform, light oil or the like. However, the organic solution used in the present invention is not limited to those solution.

The acid aqueous solution may be used as the treating liquid for isolating the biomolecule from the biological sample. The acid aqueous solution used in the present invention may be hydrochloric acid, sulfuric acid, nitric acid or the like. However, the acid aqueous solution used in the present invention is not limited to those solution.

The alkaline aqueous solution may be used as the treating liquid for isolating the biomolecule from the biological sample. The alkaline aqueous solution used in the present invention may be sodium hydroxide, potassium hydroxide, ammonium hydroxide or the like. However, the alkaline aqueous solution used in the present invention is not limited to those solution.

The treating liquid for isolating the biomolecule from the biological sample may contain chelating agent such as EDTA, EGTA or the like. However, the chelating agent used in the present invention is not limited to those solution.

The treating liquid for isolating the biomolecule from the biological sample may contain chaotropic agent such as guanidine hydrochloride acid, guanidine thiocyanate or the like. However, the chaotropic agent used in the present invention is not limited to those solution.

The treating liquid for isolating the biomolecule from the biological sample may be any combination of the aforesaid solution and the present invention is not limited to the aforesaid solution.

As described above, according to the present invention, it is possible to realize the biological sample automatic processing apparatus which includes the temperature adjuster for performing such a temperature processing of keeping, at the constant temperature during the constant time period, the sample solution containing the treating liquid such as enzyme solution, detergent solution, organic solution, acid aqueous solution, alkaline aqueous solution or the like for isolating biomolecule from a biological sample, and the mechanism for automatically moving the biological sample for the automatic processing.

Further, according to the present invention, it becomes possible to perform quickly and with high accuracy such a temperature processing of keeping the sample solution at the constant temperature during the constant time period, and to arrange the apparatus with simple configuration and cheap cost, so that such a biological sample automatic processing apparatus can be realized that can isolate biomolecule from a biological sample with high efficiency.

What is claimed is:

1. A biological sample processing apparatus, comprising:
   a temperature adjuster for keeping a plurality of holders at a set temperature while moving said plurality of holders each supporting a container receiving biological sample solution therein; and
   at least one temperature compensation section which, in a stage before a new holder moves into said temperature adjuster, controls temperature of said plurality of holders for a constant time period so as to be higher than a set temperature when said set temperature is higher than a temperature in said stage, and controls the temperature of said plurality of holders for a constant time period so as to be lower than the set temperature when said set temperature is lower than a temperature in said stage, wherein said at least one temperature compensation section can control the temperature of said plurality of holders independently from said temperature adjuster, and wherein said plurality of holders are disposed within said temperature adjuster in a closely contacted state from one another.

2. A biological sample processing apparatus according to claim 1, further comprising a pipetting means for dispensing treating liquid within the containers, wherein the apparatus repeatedly performs for an arbitrary number of times a process of dispensing the treating liquid within the containers, a process of moving the holders and a process of keeping the containers at a constant temperature for a constant time period.

3. A biological sample processing apparatus according to claim 1, wherein the at least one temperature compensation section controls a temperature of the holders in correspondence with a movement of the new holder.

4. A biological sample processing apparatus according to claim 2, wherein the treating liquid contains detergent.

5. A biological sample processing apparatus according to claim 2, wherein the treating liquid contains sodium hydroxide, potassium hydroxide or ammonium hydroxide.

6. A biological sample processing apparatus according to claim 2, wherein the treating liquid contains lysozyme, pronase or lipase.

7. A biological sample processing apparatus according to claim 2, wherein the treating liquid contains chelating agent.

8. A biological sample processing apparatus according to claim 1, wherein the treating liquid is a mixture of sodium hydroxide, potassium hydroxide and ammonium hydroxide, or a mixture of lysozyme, pronase and lipase.

9. A biological sample processing apparatus according to claim 2, wherein the treating liquid contains chaotropic reagent.

10. A biological sample processing apparatus according to claim 1, wherein the biological sample contains microorganism.

11. A biological sample processing apparatus according to claim 1, wherein the microbe is mycobacteriaceae.

* * * * *